US010193313B2

(12) United States Patent
Burrows

(10) Patent No.: US 10,193,313 B2
(45) Date of Patent: Jan. 29, 2019

(54) FLEXIBLE CONTROL SYSTEM FOR CORONA IGNITION POWER SUPPLY

(71) Applicant: Federal-Mogul Ignition Company, Southfield, MI (US)

(72) Inventor: John Antony Burrows, Timperly (GB)

(73) Assignee: Federal-Mogul Ignition LLC, Southfield, MI (US)

( * ) Notice: Subject to any disclaimer, the term of this patent is extended or adjusted under 35 U.S.C. 154(b) by 921 days.

(21) Appl. No.: 14/568,219

(22) Filed: Dec. 12, 2014

(65) Prior Publication Data

US 2015/0171600 A1 Jun. 18, 2015

Related U.S. Application Data

(60) Provisional application No. 61/915,088, filed on Dec. 12, 2013, provisional application No. 61/931,131, (Continued)

(51) Int. Cl.
*F02P 5/15* (2006.01)
*F02P 23/04* (2006.01)
(Continued)

(52) U.S. Cl.
CPC ............ *H01T 19/00* (2013.01); *F02P 5/1502* (2013.01); *F02P 23/04* (2013.01); *G01M 15/02* (2013.01);
(Continued)

(58) Field of Classification Search
CPC .................................. H01T 15/00; H01T 19/00
See application file for complete search history.

(56) References Cited

U.S. PATENT DOCUMENTS

| 4,208,992 A | 6/1980 | Polo |
| 5,149,940 A | 9/1992 | Davis et al. |

(Continued)

FOREIGN PATENT DOCUMENTS

| CN | 101351638 A | 1/2009 |
| CN | 101743395 A | 6/2010 |

(Continued)

OTHER PUBLICATIONS

International Search Report, dated Mar. 25, 2015 (PCT/US2014/069952).

(Continued)

*Primary Examiner* — Ronald W Leja
*Assistant Examiner* — Christopher Clark
(74) *Attorney, Agent, or Firm* — Robert L. Stearns; Dickinson Wright, PLLC

(57) ABSTRACT

A corona ignition system including a corona igniter, switches, and a programmable controller capable of rapidly adjusting to changes in resonant frequency is provided. Energy at a drive frequency and an output current is provided to the corona igniter. Switches provide energy to the corona igniter at the drive frequency and are activated at different times. The controller obtains the output current provided to the corona igniter, typically once every half cycle, and activates the first switch a predetermined amount of time after a first zero crossing of the output current, wherein the first zero crossing is a zero crossing of the most recent full cycle of the output current. The second switch is activated a predetermined amount of time after a second zero crossing occurring after the first zero crossing. The delay of the system is accounted for by the controller, rather than other components.

20 Claims, 10 Drawing Sheets

Related U.S. Application Data filed on Jan. 24, 2014, provisional application No. 61/950,991, filed on Mar. 11, 2014, provisional application No. 62/072,530, filed on Oct. 30, 2014, provisional application No. 62/090,096, filed on Dec. 10, 2014.

(51) Int. Cl.

| | | |
|---|---|---|
| *H01T 19/00* | (2006.01) | |
| *G01M 15/02* | (2006.01) | |
| *G01N 27/02* | (2006.01) | |
| *H01T 15/00* | (2006.01) | |
| *H02M 3/00* | (2006.01) | |
| *F02P 3/04* | (2006.01) | |
| *F02P 17/00* | (2006.01) | |

(52) U.S. Cl.
CPC ............. *G01N 27/02* (2013.01); *H01T 15/00* (2013.01); *H02M 3/00* (2013.01); *F02N 2300/2011* (2013.01); *F02P 3/0407* (2013.01); *F02P 17/00* (2013.01)

(56) References Cited

U.S. PATENT DOCUMENTS

| | | | |
|---|---|---|---|
| 5,179,928 | A | 1/1993 | Cour et al. |
| 5,361,737 | A | 11/1994 | Smith et al. |
| 5,513,618 | A | 5/1996 | Rich et al. |
| 5,568,801 | A | 10/1996 | Paterson et al. |
| 6,758,199 | B2 | 7/2004 | Masters et al. |
| 6,883,507 | B2 | 4/2005 | Freen |
| 7,956,543 | B2 | 6/2011 | Agneray et al. |
| 7,974,068 | B2 | 7/2011 | Agneray et al. |
| 8,342,147 | B2 | 1/2013 | Nouvel et al. |
| 8,547,020 | B2 | 10/2013 | Barroso et al. |
| 8,552,651 | B2 | 10/2013 | Sugino et al. |
| 8,567,372 | B2 | 10/2013 | Visser et al. |
| 8,578,902 | B2 | 11/2013 | Permuy et al. |
| 8,800,539 | B2 | 8/2014 | Toedter et al. |
| 8,869,765 | B2 | 10/2014 | Braeuchle |
| 2004/0129241 | A1 | 7/2004 | Freen |
| 2008/0011281 | A1* | 1/2008 | Kraus ............... F02P 3/051 123/623 |
| 2009/0122583 | A1 | 5/2009 | Gelerter |
| 2009/0194051 | A1 | 8/2009 | Smith et al. |
| 2009/0201027 | A1* | 8/2009 | Sexton ............... H02H 11/002 324/527 |
| 2009/0229581 | A1 | 9/2009 | Ikeda |
| 2010/0116257 | A1 | 5/2010 | Agneray et al. |
| 2010/0229639 | A1 | 9/2010 | Agneray et al. |
| 2010/0251995 | A1 | 10/2010 | Nouvel et al. |
| 2010/0263643 | A1* | 10/2010 | Agneray ............ F02P 9/007 123/608 |
| 2010/0282198 | A1 | 11/2010 | Hampton et al. |
| 2010/0313841 | A1 | 12/2010 | Agneray et al. |
| 2011/0114071 | A1 | 5/2011 | Freen |
| 2011/0146607 | A1 | 6/2011 | Smith et al. |
| 2011/0175691 | A1 | 7/2011 | Smith et al. |
| 2011/0253114 | A1 | 10/2011 | Schremmer |
| 2011/0297132 | A1 | 12/2011 | Schremmer et al. |
| 2011/0305998 | A1 | 12/2011 | Toedter et al. |
| 2012/0055430 | A1 | 3/2012 | Braeuchle |
| 2012/0055455 | A1 | 3/2012 | Ruan et al. |
| 2012/0063054 | A1 | 3/2012 | Burrows et al. |
| 2012/0145136 | A1 | 6/2012 | Burrows et al. |
| 2012/0180742 | A1 | 7/2012 | Burrows |
| 2012/0249006 | A1 | 10/2012 | Burrows |
| 2012/0249163 | A1 | 10/2012 | Burrows |
| 2013/0208393 | A1 | 8/2013 | Hampton et al. |
| 2013/0300474 | A1 | 11/2013 | Chang et al. |
| 2013/0308347 | A1 | 11/2013 | Sato et al. |
| 2014/0226252 | A1 | 8/2014 | Freen |

FOREIGN PATENT DOCUMENTS

| | | |
|---|---|---|
| CN | 102562412 A | 7/2012 |
| CN | 102804527 A | 11/2012 |
| CN | 103597202 A | 2/2014 |
| DE | 19747701 A1 | 5/1999 |
| DE | 102005036968 A1 | 2/2007 |
| DE | 102010062304 A1 | 6/2012 |
| DE | 102010062305 A1 | 6/2012 |
| JP | 2013019301 A | 1/2013 |
| WO | 2010011838 A1 | 1/2010 |
| WO | 2012138674 A1 | 10/2012 |

OTHER PUBLICATIONS

International Search Report, dated Mar. 25, 2015 (PCT/US2014/069947).

International Search Report, dated Mar. 25, 2015 (PCT/US2014/069958).

International Search Report, dated Mar. 25, 2015 (PCT/US2014/069974).

* cited by examiner

FLEXIBLE CONTROL SYSTEM FOR CORONA IGNITION POWER SUPPLY

CROSS-REFERENCE TO RELATED APPLICATIONS

This U.S. patent application claims the benefit of U.S. provisional patent application No. 61/915,088, filed Dec. 12, 2013; U.S. provisional patent application No. 61/931,131, filed Jan. 24, 2014; U.S. provisional patent application No. 61/950,991, filed Mar. 11, 2014; U.S. provisional patent application No. 62/072,530, filed Oct. 30, 2014; and U.S. provisional patent application No. 62/090,096, filed Dec. 10, 2014, the entire contents of each being incorporated herein by reference in their entirety.

BACKGROUND OF THE INVENTION

1. Field of the Invention

This invention relates generally to a corona discharge ignition system, and more particularly to a corona discharge ignition system for controlling energy supplied to the system.

2. Related Art

Corona discharge ignition systems provide an alternating voltage and current, reversing high and low potential electrodes in rapid succession which enhances the formation of corona discharge and minimizes the opportunity for arc formation. The system includes a corona igniter with a central electrode charged to a high radio frequency voltage potential and creating a strong radio frequency electric field in a combustion chamber. The electric field causes a portion of a mixture of fuel and air in the combustion chamber to ionize and begin dielectric breakdown, facilitating combustion of the fuel-air mixture, which is referred to as an ignition event. The electric field is preferably controlled so that the fuel-air mixture maintains dielectric properties and corona discharge occurs, also referred to as a non-thermal plasma. The ionized portion of the fuel-air mixture forms a flame front which then becomes self-sustaining and combusts the remaining portion of the fuel-air mixture. Preferably, the electric field is controlled so that the fuel-air mixture does not lose all dielectric properties, which would create a thermal plasma and an electric arc between the electrode and grounded cylinder walls, piston, metal shell, or other portion of the igniter. An example of a corona discharge ignition system is disclosed in U.S. Pat. No. 6,883,507 to Freen.

In addition, the corona discharge ignition system is preferably controlled so that energy is provided to the corona igniter at a drive frequency equal or close to the resonant frequency of the corona igniter. However, achieving this level of control is difficult, especially at a wide range of frequencies. Changes in the resonant frequency during operation, for example due to arcing events, also make it difficult to achieve the desired resonant frequency control.

SUMMARY OF THE INVENTION

One aspect of the invention provides a corona discharge ignition system including a corona igniter, switches, and a controller capable of operating at a wide range of resonant frequencies and capable of making immediate adjustments to the drive frequency, for example in response to resonant frequency changes, in order to maintain the drive frequency equal to or very close to the resonant frequency of the corona igniter. The corona igniter receives energy at a drive frequency and output current. A first switch and a second switch provide energy to the corona igniter at the drive frequency. The controller obtains the phase of the output current and activates the first switch a predetermined amount of time after a zero crossing of the output current while the second switch is not activated. The zero crossing is a zero crossing of any previous full cycle of the output current.

Another aspect of the invention provides a method of controlling the corona discharge ignition system including the corona igniter, switches, and controller. The method includes obtaining the phase of the output current; and activating the first switch a predetermined amount of time after a zero crossing of the output current while the second switch is not activated. The zero crossing is a zero crossing of a previous full cycle of the output current.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION

Figure 1:
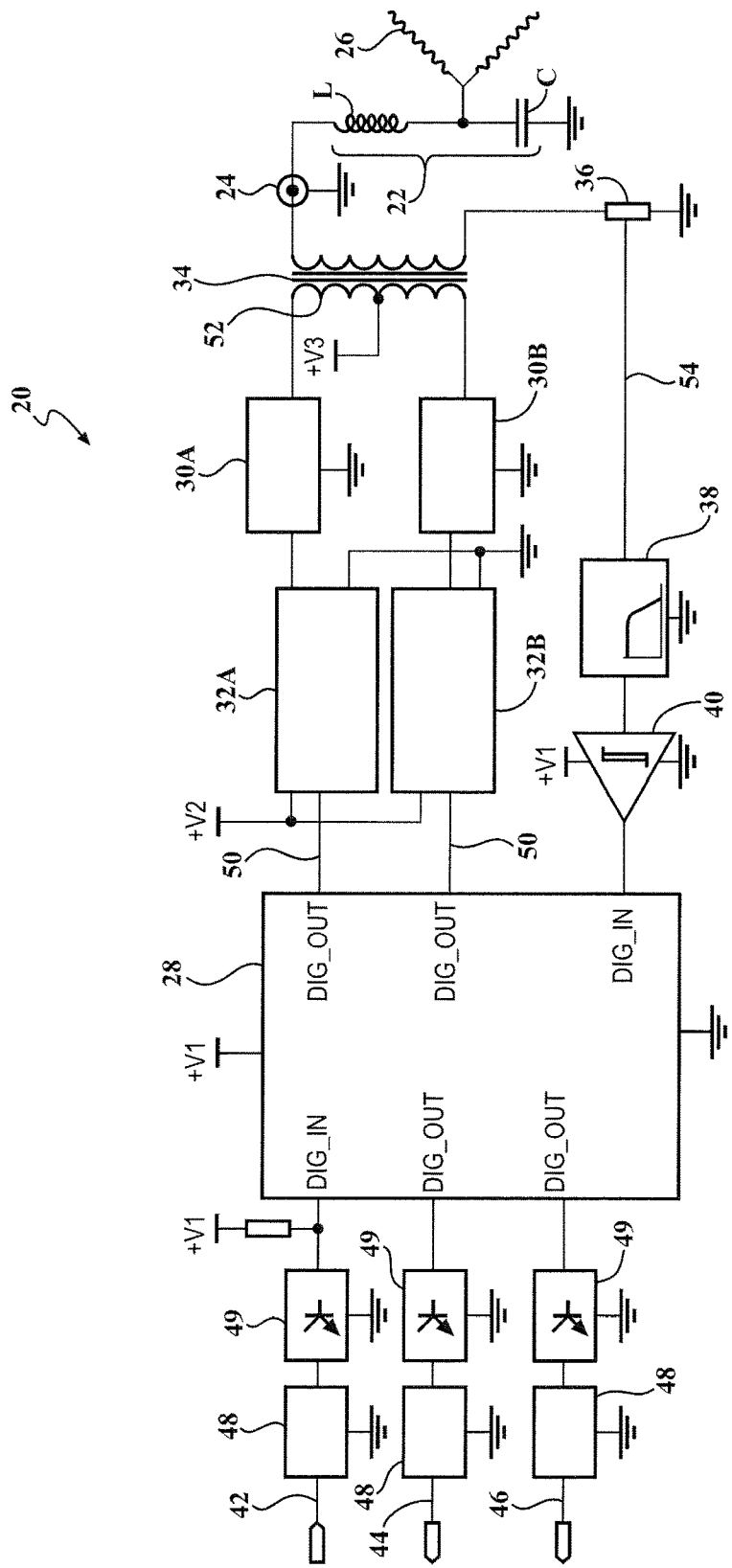
FIG. 1 is a block diagram of a corona discharge ignition system according to a first exemplary embodiment of the invention.

The present invention provides improved operation of a corona discharge ignition system 20 for an internal combustion engine application. Exemplary embodiments of the system 20 are shown in FIGS. 1-10. In each embodiment, the system 20 includes a corona igniter 22 operating at a resonant frequency. Energy at a drive frequency and an output current is provided to the corona igniter 22. The phase of the output current can be measured at an input the corona igniter 22, which is also referred to as the output 24 of a transformer 34. The corona igniter 22 preferably forms a high radio frequency electric field at a firing end, referred to as corona discharge 26, to ignite a mixture of fuel and air in a combustion chamber of the engine. The system 20 also includes a controller 28 and at least one pair of switches 30A, 30B and/or 30C and 30D that control the drive frequency provided to the corona igniter 22, and the capacitance/inductance circuit of the system 20, so that the drive frequency is maintained at the resonant frequency of the corona igniter 22. Operating the system 20 such that the drive frequency is equal to or close to the resonant frequency provides voltage amplification leading to robust corona discharge 26 in the combustion chamber.

Other methods currently used to maintain the drive frequency at the resonant frequency of the corona igniter in comparative systems include making a low-power measurement of the igniter current while applying different drive frequencies; measuring voltage or current (or a proxy thereof) of the corona igniter and varying frequency to maximize the same; or implementing a phase-locked-loop (PLL) to keep voltage and current in phase at the input to the resonator, which is the condition required for resonance. However, all of these methods have potential problems during operation. Methods which adjust frequency to maximize an electrical parameter require constant adjustment of the frequency, referred to as "hunting," to be sure they are running at the resonant frequency. A significant amount of time is required before the resonant frequency is identified. Also, formation of an arc, whether intentional or accidental, causes a phase change in the current of energy which is very difficult for these typical systems to follow. In addition, the output voltage may collapse for many tens or hundreds of cycles while the controller acquires the proper frequency again. Systems relying on a phase-locked-loop do not suffer from "hunting," but inherently require some damping of their response to achieve stability. This makes acquisition of the resonant frequency relatively slow, and formation of an arc causes a phase change which cannot be followed easily, leading to a temporary collapse of energy at the input of the corona igniter.

The system 20 of the present invention avoids those problems and can continuously operate at a drive frequency which is equal to, or very close to, the resonant frequency of the corona igniter 22. This continuous operation is achieved by measuring, or otherwise obtaining, a measurement of the phase of the output current to the corona igniter 22 and providing that information about the output current to the controller 28. Preferably, the phase of the output current is obtained once every half cycle and provided to the controller 28 once every half cycle. The output current measurements are obtained at the input 24, and the resonant frequency of the corona igniter 22 can be obtained from the phase of the output current at every half cycle. The controller 28 analyzes the information about the output current and activates one of the switches 30A or 30B, for example the first switch 30A, a predetermined amount of time after a first zero crossing of the output current. If the system includes four switches, then the controller activates switches 30A and 30D simultaneously, or activates switches 30B and 30C simultaneously.

Preferably, the first zero crossing is one of the zero crossings of the most recent full cycle of the output current. However, the first zero crossing could be one of the zero crossings of any of the previous full cycles of the output current. Depending on the phase of the output current provided to the controller 28, the first zero crossing of the last full cycle can be selected from two positive zero crossings and one negative zero crossing, or two negative zero crossings and one positive zero crossing. The controller 28 then activates the other switch 30A or 30B, in this case the second switch 30B, a predetermined amount of time after a second zero crossing of the output current, wherein the second zero crossing occurs after the first zero crossing. When one of the switches 30A or 30B is active, energy can flow from a power supply (not shown) through the active switch 30A or 30B to the corona igniter 22. When the switches 30A, 30B are not activated, energy cannot flow through to the corona igniter 22. Although the switch 30A is referred to as the first switch, and the switch 30B is referred to as the second switch, the switch 30B could alternatively be referred to as the first switch, and the switch 30A could be referred to as the second switch.

The controller 28 can use various different methods to determine the predetermined amount of time between the selected zero crossing and activation of the switch 30A or 30B. In one embodiment, the predetermined amount of time between the selected first zero crossing or second zero crossing and activation of the one switch 30A or 30B by the controller 28 is fixed and programmed into the controller 28. This is often the case when the resonant frequency of the system 20 is within a fixed range of frequencies. In another embodiment, the controller 28 uses an algorithm, also programmed into the controller 28, to determine the predetermined amount of time. In yet another embodiment, the controller 28 analyzes previous cycles of the output current to determine the predetermined amount of time between the selected first zero crossing or second zero crossing and activation of the switch 30A or 30B.

In each case, only one of the switches 30A or 30B is active and providing energy to the corona igniter 22 at any given time during operation of the corona ignition system 20. Thus, the controller 28 deactivates the first switch 30A before activating the second switch 30B, and vice versa, so that the two switches 30A, 30B are not active at the same time. For example, the first switch 30A is active and thus provides energy to the corona igniter 22 whenever the output current is positive, and the second switch 30B is active and thus provides energy to the corona igniter 22 whenever the output current is negative. Preferably, activation of the switches 30A, 30B is synchronized with the resonant frequency of the corona igniter 22, so that one switch 30A or 30B is activated by the controller 28 each time the output current provided to the corona igniter 22 crosses through zero. In this case, the drive frequency provided to the corona igniter 22 is equal to, or approximately equal to, the resonant frequency of the corona igniter 22.

Numerous advantages are provided by the system 20 and method of the present invention. First, the system 20 can make immediate adjustments to the drive frequency, for example in response to resonant frequency changes, in order to maintain the drive frequency equal to, or very close to, the resonant frequency of the corona igniter 22. The system 20 is also able to efficiently track and respond to phase changes of the current in the corona igniter 22 during arcing events. Near-immediate acquisition of the resonant frequency and rapid real-time adjustment of the drive frequency is possible to maintain the best possible performance. In other words, the system 20 maintains a very rapid lock, which means that the voltage supplied to the system 20 follows the sinusoidal changes in the frequency of the current in the corona igniter 22. Furthermore, the system 20 is able to operate at a much wider range of frequencies, compared to other systems.

It should be understood that the system 20 operates at "resonant frequency" when the voltage and current supplied to the corona igniter 22 have the same frequency and are in phase. The term "cycle" means one complete period of the sinusoidal output of voltage or current from the corona igniter 22, also referred to as one complete period of oscillation. The term "half-cycle" means half of that period, or one half of the period of oscillation. It is also noted that methods of resonant frequency control which can employ the system described herein are disclosed in related U.S. patent application Ser. Nos. 14/568,266, 14/568,330, and 14/568,438, each listing the same inventor and filed on the same day as the present application.

FIG. 1 is a block diagram of the corona discharge ignition system 20 according to a first exemplary embodiment which is capable of providing a rapid response to resonant frequency changes and arc formation, in order to maintain the drive frequency equal to or approximately equal to the resonant frequency of the corona igniter 22. In addition to the controller 28, switches 30A, 30B, and corona igniter 22, the system 20 also includes a pair of drivers 32A, 32B, referred to as a first driver 32A and a second driver 32B. The system 20 of FIG. 1 further includes a transformer 34, a first current sensor 36, a first low-pass filter 38, and a first signal conditioner 40. The current provided to and received by the corona igniter 22 is equal to the current at the input 24, and the phase of that current is measured at the input 24 by the first current sensor 36.

The system 20 is controlled by the controller 28, which is preferably a programmable digital or mixed-signal controller, such as a digital signal processor (DSP), complex programmable logic device (CPLD), field-programmable gate array (FPGA), microcontroller, or microprocessor. The controller 28 receives a trigger input signal 42 which commands the controller 28 to initiate the production of corona discharge 26 in the combustion chamber. The controller 28 also provides an arc detect output signal 44 to inform any external control system (not shown) that an arc has been detected, and a feedback output signal 46 to provide additional data about the health and operation of the circuit to any external control system. The trigger input signal 42, arc detect output signal 44, and feedback output signal 46 conveyed to and from the controller 28 are filtered by electromagnetic compatibility filters, referred to as EMC filters 48, and other protection components 49. In response to the trigger input signal 42, the controller 28 provides drive signals 50 to the drivers 32A, 32B which control the switches 30A, 30B. When one of the switches 30A or 30B is active, a DC voltage V3 is applied to a primary winding 52 of the transformer 34. The transformer 34 then provides energy through the input 24 and to the corona igniter 22 at the drive frequency. In the exemplary embodiment, the transformer 34 has a configuration known in the art as a "push-pull" configuration.

In the system 20 of FIG. 1, the current provided to the corona igniter 22 (the output current), is measured at the first current sensor 36 using any suitable technique, such as a shunt resistor, hall-effect sensor, or current transformer. A current output signal 54, including a measurement of the phase of the current provided to the corona igniter 22, is conveyed from the first current sensor 36 toward the controller 28. Preferably, this current output signal 54 is lightly filtered by the first low-pass filter 38 before being conveyed to the controller 28. The first low-pass filter 38 creates a phase shift in the current output signal 54 which is smaller than the period of oscillation of the current. In one embodiment, the phase shift is 180 degrees, but preferably the phase shift is less than 180 degrees, and more preferably the phase shift is less than 90 degrees, which is less than one half cycle. The first low-pass filter 38 also removes unwanted high frequency noise generated by switching high current and voltages. The filtered current output signal 54 is then transferred to the first signal conditioner 40, which makes the current output signal 54 safe for transferring to the controller 28. Thus, the current output signal 54 is at a level that can be safely handled by the controller 28. Typically, the only information contained in the current output signal 54 is the phase of the current provided to the corona igniter 22 at the input 24.

The controller 28 receives the current output signal 54 with the current measurement obtained by the first current sensor 36 and uses the current measurement to identify the resonant frequency of the corona igniter 22 and the optimum timing for activating the switches 30A, 30B to give resonant operation. The phase of the output current is provided to the controller 28, preferably once every half cycle. In the exemplary embodiment, once the controller 28 determines the timing of the first switch 30A or second switch 30B to be activated, the controller 28 instructs the first driver 32A to activate the first switch 30A or instructs the second driver 32B to activate the second switch 30B. The drivers 32A, 32B are instructed to activate the switches 30A, 30B at the predetermined times, so that the drive frequency of the energy conveyed through the switches 30A, 30B to the transformer 34 and ultimately to the corona igniter 22 is equal to, or approximately equal to, the resonant frequency of the corona igniter 22.

As discussed above, this resonant frequency operation is preferably obtained by activating one of the switches 30A or 30B each time the output current to the corona igniter 22 crosses through zero. When the switches 30A, 30B are activated at such times, the drive frequency is equal to, or approximately equal to, the resonant frequency of the corona igniter 22. The controller 28 first determines the time at which the first switch 30A should be activated by analyzing the phase of the output current provided in the current output signal 54. The controller 28 identifies a first zero crossing of the output current and activates the first switch 30A a predetermined amount of time after this first zero crossing. The first zero crossing is one of the zero crossings of the most recent full cycle of the output current, or one of the zero crossings taken from any of the previous full cycles. Depending on the phase of the output current provided to the controller 28 in the output signal 54, the first zero crossing of the most recent full cycle (or any previous cycle) can be selected from two positive zero crossings and one negative zero crossing, or from two negative zero crossings and one positive zero crossing.

The controller 28 also analyzes the phase of the output current provided in the current output signal 54 to activate the second switch 30B at the correct time to achieve resonant frequency operation. The second switch 30B is preferably activated a predetermined amount of time after a second zero crossing of the output current. The second zero crossing occurs any time after the first zero crossing.

Also as discussed above, the controller 28 can use various different methods to determine the predetermined amount of time between the selected zero crossing and activation of the one switch 30A or 30B. In other words, the controller 28 can use various different methods to determine and set the delay between the selected zero crossing and activation of the one switch 30A or 30B. In one embodiment, the predetermined amount of time between the selected first zero crossing or the selected second zero crossing and activation of the first switch 30A or second switch 30B is fixed and programmed into the controller 28. This is often the case when the drive frequency is within a fixed, limited range of frequencies. In another embodiment, the controller 28 analyzes previous cycles of the output current to determine the predetermined amount of time between the selected first zero crossing or second zero crossing and activation of the one switch 30A or 30B.

In yet another embodiment, the controller 28 uses an algorithm, programmed into the controller 28, to determine the predetermined amount of time between the select zero crossing and activation of the switch 30A or 30B. The algorithm determines the difference between the expected zero crossing of the output current and the actual zero crossing of the output current, which is measured at the input 24 by the first current sensor 36 during a previous cycle. The expected zero crossing is the time at which the controller 28 expects the output current to cross through zero, and it is typically a predetermined duration of time after one of the switches 30A or 30B is activated. This difference in time between the expected and actual zero crossing occurs due to the delay in the components of the system 20. The controller 28 then uses the information about the delay to determine the time at which the switch 30A or 30B should be activated, so that the switch 30A or 30B is activated at the same time the output current crosses through zero.

It is important that only one switch 30A or 30B is active at any given time during operation of the system 20. For example, the controller 28 can activate the first driver 32A which in turn activates the first switch 30A at a time when the output current crosses through zero. Next, the controller 28 turns off the first driver 32A and the first switch 30A, and then activates the second driver 32B, which in turn activates the second switch 30B the next time that the output current crosses through zero. The controller 28 can analyze each current output signal 54 received from the first signal conditioner 40 and can adjust the timing of the switches 30A, 30B whenever needed.

Another advantage of the corona ignition system 20 of FIG. 1 is that the first low-pass filter 38 can operate at a wide range of frequencies and can produce a delay of any length. In other words, the predetermined amount of time between the selected zero crossing and the time at which one of the switches 30A or 30B is activated can be of any length. The first low-pass filter 38 is not compromised by the requirement to produce a predefined delay, like filters of comparative corona discharge ignition systems. The first low-pass filter 38 can be of optimum design for phase shift and frequency response, and can be selected based on its size, cost, or ability to reduce noise, rather than its ability to provide a predefined delay.

In the inventive system 20, a delay caused by the first low-pass filter 38 is known, and the controller 28 can be programmed to account for the delay of the first low-pass filter 38, along with the delay of other components in the circuit, in order to convey the drive signals 50 to the drivers 32 at the correct instant to provide proper resonance. The delay of the first low-pass filter 38 is typically less than one cycle, and preferably less than one half cycle. Unlike comparative systems, the controller 28, rather than other components, causes the majority of the loop delay between the current crossing zero at the input 24 of the corona igniter 22 and the switches 30A, 30B being activated. The controller 28 can adjust the loop delay, and the loop delay can be adjusted over almost any desired range of frequencies. In this system 20, the delay is taken out of the first low-pass filter 38 and put into control software of the controller 28. Thus, the delay is not limited to a predefined delay, such as 500 nanoseconds per half cycle as in comparative systems. The controller 28 can also constantly adjust the loop delay, and thus the loop delay does not depend on the resonant frequency of the system 20. The timing of the switches 30A, 30B can be adjusted in view of the known loop delay so that the switches 30A, 30B are activated and provide energy to the transformer 34 when current measured by the first current sensor 36 at the input 24 crosses through zero.

A number of benefits are achieved by the combination of the programmable controller 28, which determines the optimum timing for the activation of switches 30A, 30B and the first low-pass filter 38, which provides a phase shift less than a period of the resonant frequency. First, the system 20 can operate over a very wide frequency range. There is effectively no lower limit to the operating frequency. The highest operating frequency is only limited by the sum of the delays caused by the first low-pass filter 38, first signal conditioner 40, drivers 32A, 32B, switches 30A, 30B, and transformer 34, and thus the upper limit is typically many megahertz. In addition, the dead-time (time immediately before and after the zero crossing) of the system 20 may be reduced to increase output voltage of the corona igniter 22 by an effective increase in duty cycle. Also, energy stored in the transformer 34 and switching closer to the actual zero crossing of the current in the corona igniter 22 reduces energy losses in the switches 30A, 30B. Other benefits include the ability to vary dead-time based on the operating conditions, or the ability to measure and compare the drive frequency to predefined criteria for test and diagnosis purposes. Yet another advantage is the ability of the system 20 to easily compensate for different cable lengths (cable not shown) between the input 24 and the load, which can be important because any cable located between the input 24 and the transformer 34 can introduce an additional delay which must be compensated. The ability to compensate for this additional delay with a software change by the controller 28 makes the system 20 more flexible in use. Furthermore, as discussed above, controlling the timing of the switches 30A, 30B based on a zero crossing event of the most recent full cycle of the output current, or a previous full cycle, allows the controller 28 to provide a rapid response to resonant frequency changes and arc formation. The well-defined short time delay achieved by the programmable controller 28 and first low-pass filter 38 can be corrected in the controller 28 so that the switches 30A, 30B are controlled directly from the measured phase of the output current provided to the corona igniter 22. This removes the need to make measurements over multiple oscillations. Finally, as discussed above, the system 20 can make very rapid changes in drive frequency and phase of the current such that the system 20 continuously operates at the resonant frequency of the corona igniter 22.

Figure 2:
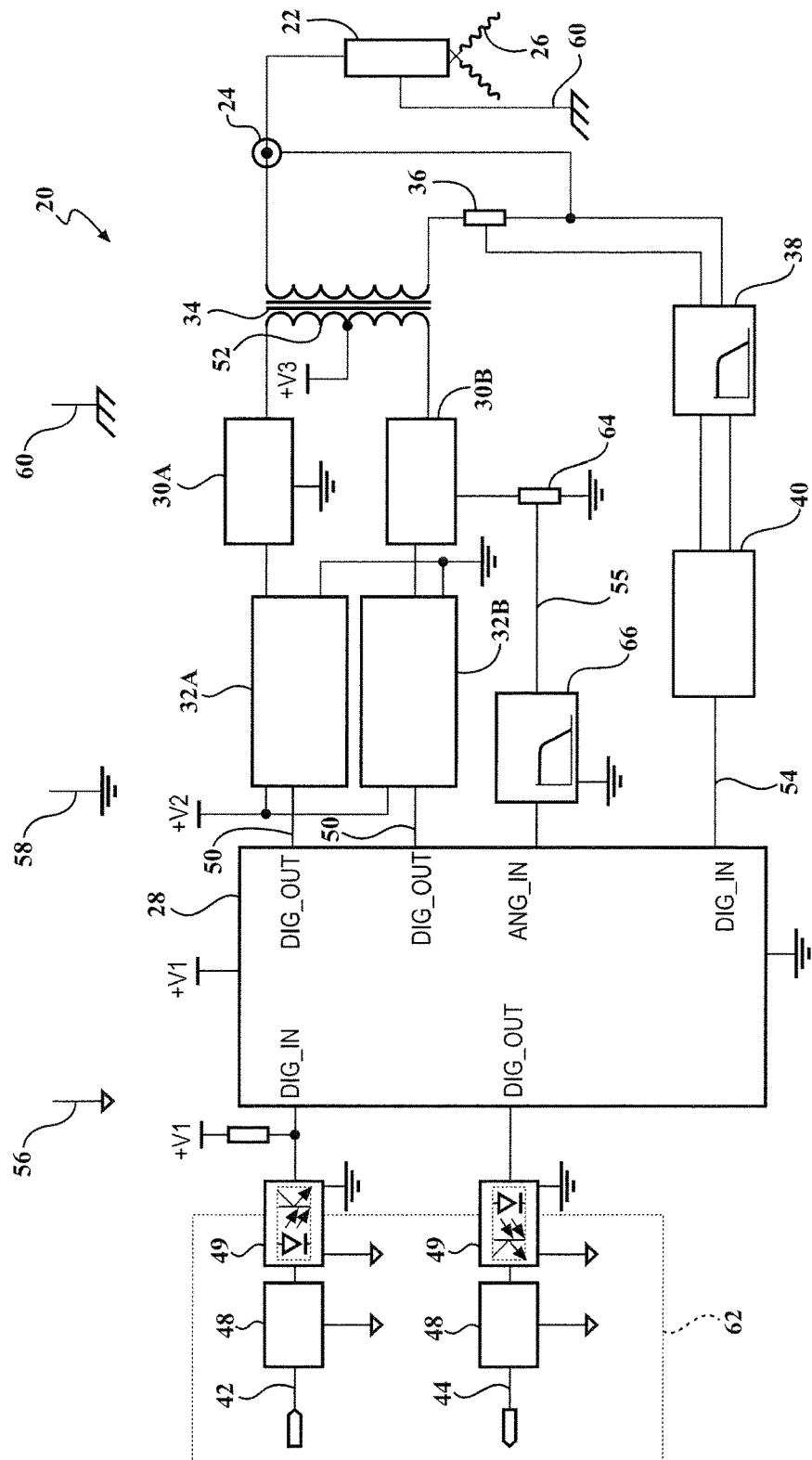
FIG. 2 is a block diagram of a corona discharge ignition system according to a second exemplary embodiment of the invention.

FIG. 2 is a block diagram of a corona discharge 26 ignition system 20 according to a second exemplary embodiment of the invention, which operates like the system 20 of FIG. 1, but includes several additional features. One additional feature is that that the various functional sections of the system 20 include a control system ground 56, a power system ground 58, and load ground 60 which are separated from one another. This technique is used to improve EMI and/or electromagnetic compatibility (EMC). The control system ground 56 is isolated from a power system ground 58 by galvanic isolation 62. The transformer 34 isolates the power system ground 58 from the load ground 60, and this isolation must be maintained between the first current sensor 36 and the controller 28. The isolation between the power system ground 58 and the load ground 60 may be achieved by adding galvanic isolation 62 at the first low-pass filter 38 or the first signal conditioner 40. Alternatively, the isolation between the power system ground 58 and the load ground 60 can be achieved by operating the first low-pass filter 38 or the first signal conditioner 40 in a differential mode where only a negligible current can flow through the device. In the system 20 of FIG. 2, only the first signal conditioner 40 operates in differential mode to isolate the power system ground 58 from the load ground 60. One or more of these methods may be employed.

Another additional feature of the system 20 of FIG. 2 is a second current sensor 64 to measure the amplitude of the current in the second switch 30B on the primary side of the transformer 34. The second current sensor 64 specifically measures the current at the output of the second switch 30B. Alternatively, there could be a second current sensor 64 at each of the switches 30A, 30B. The second current sensor 64 provides an additional feedback signal 55 to the controller 28, giving valuable diagnostic information which is not possible through the phase measurement of only the first current sensor 36. For example, it is possible to detect an open or short circuit in the load circuit by measuring the current at the output of the switches 30A, 30B. In addition, the system 20 of FIG. 2 includes a second low-pass filter 66 located between the current sensor and the controller 28 to lightly filter the current output signal 54 before providing the feedback signal 55 to the controller 28.

Figure 3:
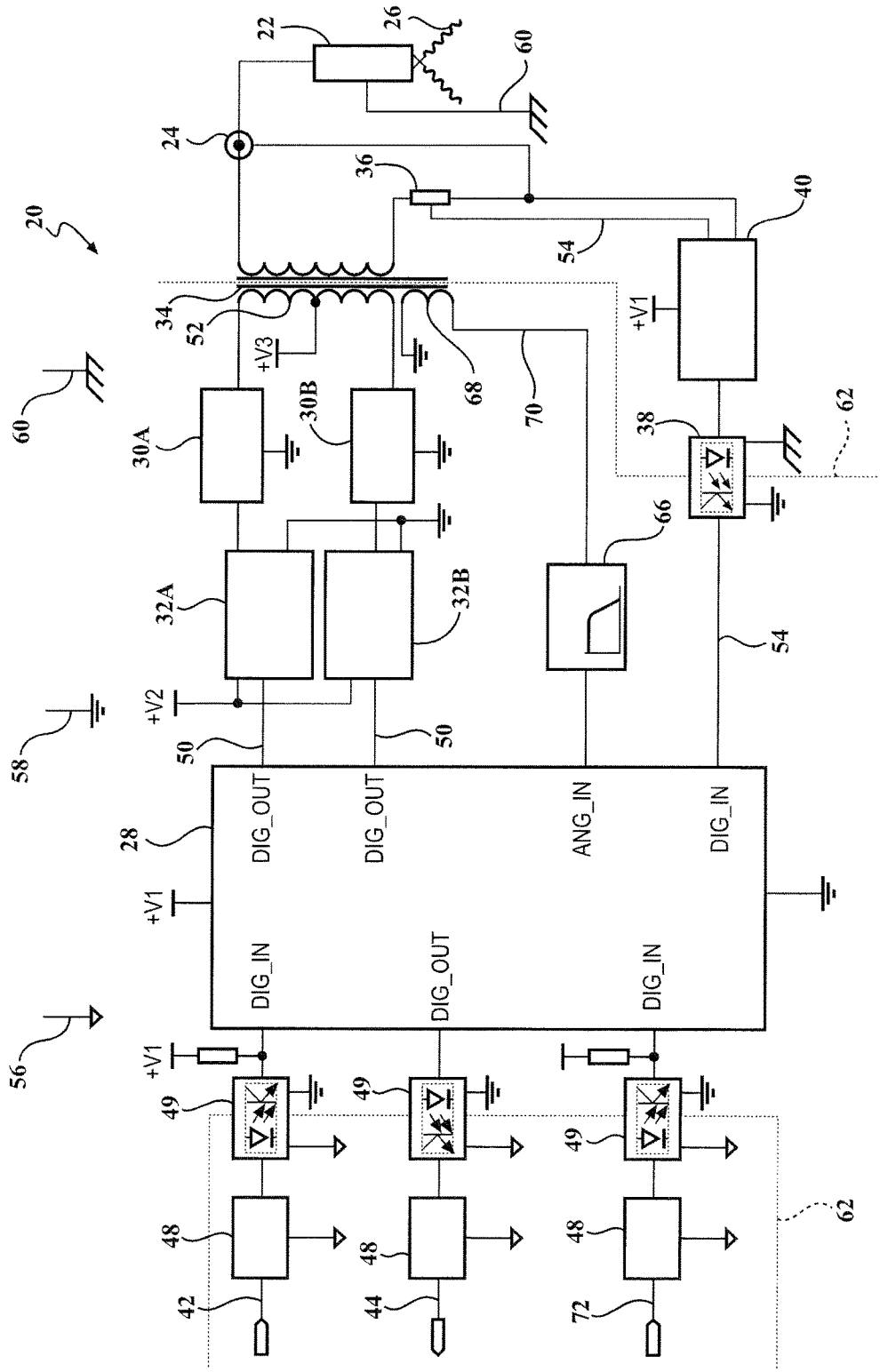
FIG. 3 is a block diagram of a corona discharge ignition system according to a third exemplary embodiment of the invention.

FIG. 3 is a block diagram of a corona discharge 26 ignition system 20 according to a third exemplary embodiment of the invention. The system 20 of FIG. 3 also includes the galvanic isolation 62, but in this embodiment, the galvanic isolation 62 is located on both the energy input and energy output sides of the controller 28, and completely separates the three grounds 56, 58, 60. One or both of the barriers provided by the galvanic isolation 62 can be omitted if the circuit is designed to operate using fewer grounds.

The system 20 of FIG. 3 further includes another winding, referred to as a voltage feedback winding 68. The current provided by the voltage feedback winding 68 reflects the voltage at the input 24 of the corona igniter 22. The actual voltage at the input 24 is measured, not just the phase proportionate to the voltage. A voltage signal 70 including the voltage data from the voltage feedback winding 68 is transferred to the controller 28 for diagnostics and control purposes. The voltage signal 70 may be sampled using a suitable intermediate circuit to limit the size of the voltage signal 70 and, if required, provide galvanic isolation 62. Sampling the voltage signal 70 at a rate higher than twice the resonant frequency allows the actual resonant frequency to be detected more accurately by the controller 28, for example using known fast Fourier transform (FFT) methods. The system 20 of FIG. 3 also includes the second low-pass filter 66 located between the transformer 34 and the controller 28 to lightly filter the voltage signal 70 before providing the voltage signal 70 to the controller 28. The voltage signal 70 can also be used to identify and correct a phase shift caused by the transformer 34, or to provide direct measurement of the delay introduced by the drivers 32A, 32B and switches 30A, 30B, as well as the transformer 34. In summary, the voltage signal 70 may be used to improve the accuracy of the controller 28. Also, unlike the systems 20 of FIGS. 1 and 2, a control signal 72 is provided to the controller 28 of FIG. 3. The control signal 72 can include any information related to operation of the corona igniter 22, such as whether arcing occurred or the desired voltage.

Figure 4:
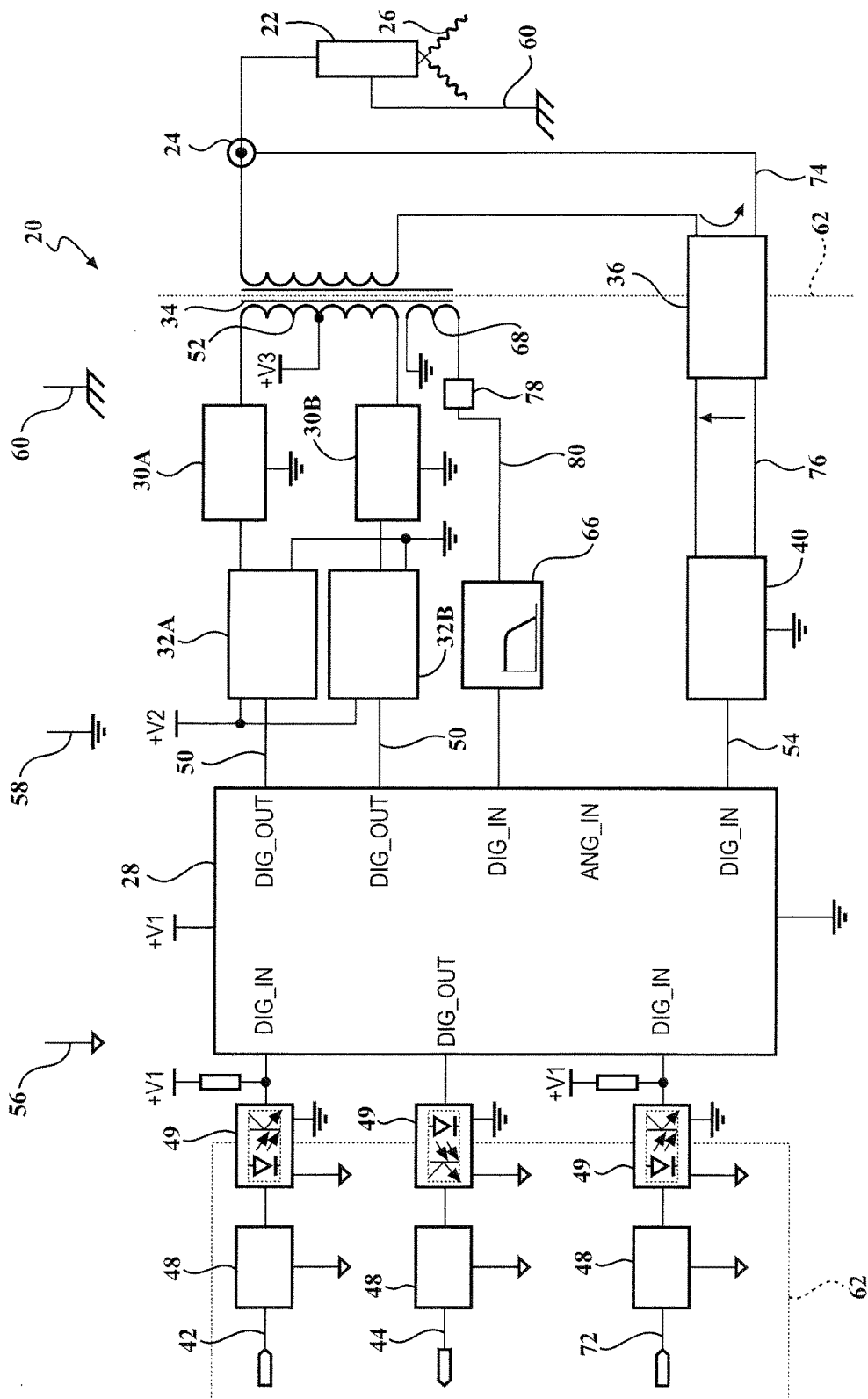
FIG. 4 is a block diagram of a corona discharge ignition system according to a fourth exemplary embodiment of the invention.

FIG. 4 is a block diagram of a corona discharge 26 ignition system 20 according to a fourth exemplary embodiment of the invention. The system 20 again includes the controller 28, drivers 32A, 32B, switches 30A, 30B, transformer 34 with the voltage feedback winding 68, input 24 to the corona igniter 22, second low-pass filter 66, first signal conditioner 40, galvanic isolation 62, and first current sensor 36. However, in this embodiment, the first current sensor 36 is an isolated four-wire device, wherein a load current 74 flowing in the load connected at the input 24 of the corona igniter 22 produces a corresponding voltage 76 which is galvanically isolated from the load circuit and hence the load ground 60. The isolated voltage 76 may be used to identify the phase of the load current 74 at the input 24 to the corona igniter 22, without any direct connection to the load circuit. The voltage 76 may be obtained from a voltage or a current source, depending on the design of the first current sensor 36. Suitable devices that can be used for the first current sensor 36 include giant magnetoresistance (GMR) current sensors, opto-isolated sensors, specialized high-side shunt measuring integrated circuits (with or without a separate shunt resistor), and current transformers. In addition, unlike the embodiment of FIG. 3, the voltage of the voltage feedback winding 68 is measured instead of the current. A voltage sensor 78 is preferably located at the output of the voltage feedback winding 68 to measure this voltage. A voltage output signal 80 is then transferred through the second low-pass filter 66 to the controller 28.

Figure 5:
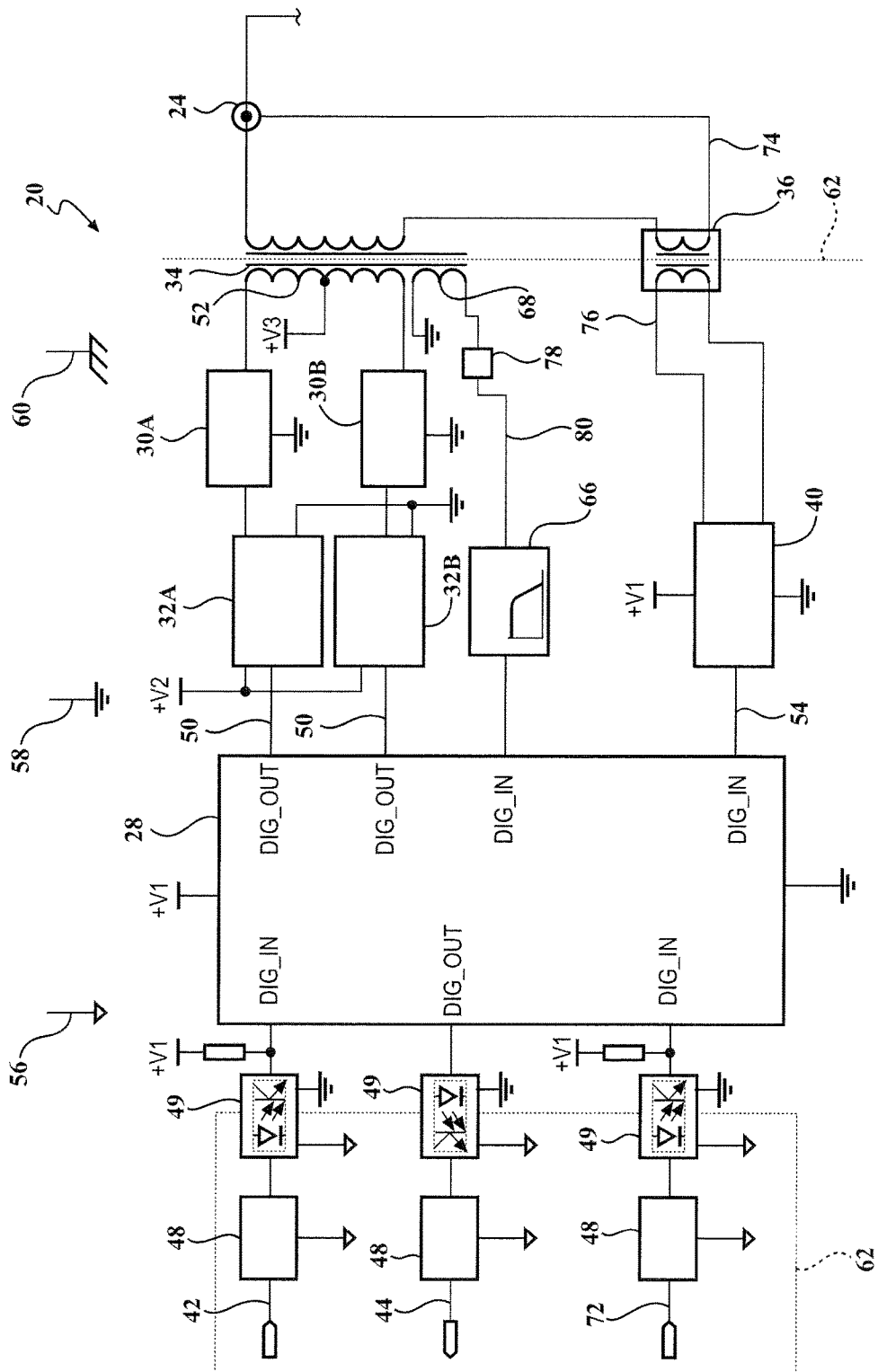
FIG. 5 is a block diagram of a corona discharge ignition system according to a fifth exemplary embodiment of the invention.

FIG. 5 is a block diagram of a corona discharge 26 ignition system 20 according to a fifth exemplary embodiment. This embodiment is similar to the embodiment of FIG. 4, except the first current sensor 36 is located between the input 24, and the first signal conditioner 40 is now a transformer, and thus referred to as a current transformer. The current transformer 36 measures the load current 74 and provides galvanic isolation 62 between the load ground 60 and the power system ground 58. The output of the current transformer 36 also generates a voltage 76 across the input impedance of the current transformer 36. Also, a separate load resistor (not shown) may optionally be used to convert the current measurement provided by the signal conditioner 40 to a corresponding voltage. The corona igniter 22 of this system and the remaining systems shown in the Figures has the same configuration as in FIGS. 2-4, although it is not shown.

Figure 6:
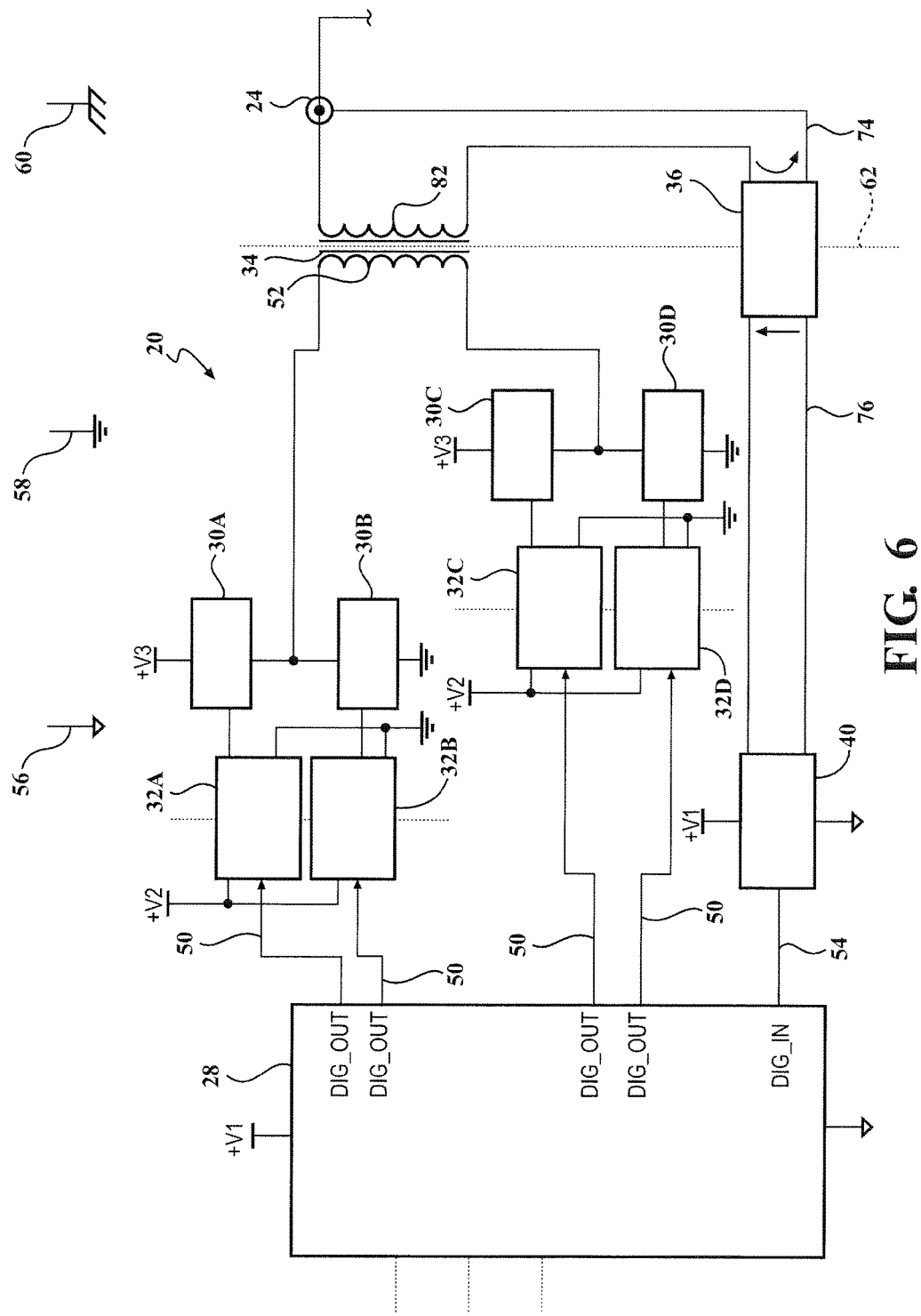
FIG. 6 is a block diagram of a corona discharge ignition system according to a sixth exemplary embodiment of the invention.

A sixth exemplary embodiment is shown in FIG. 6. The input/output signals and connections to the controller 28 are omitted for clarity, but some or all of the omitted signals and connections are still be required. In the corona ignition system 20 of this embodiment, the "push-pull" configuration of the transformer 34 is replaced by another configuration known in the art as a "full-bridge" configuration. The system 20 also includes two additional drivers 32C, 32D, each connected to an additional switch 30C, 30D. All of the drivers 32A, 32B, 32C, 32D are isolated. In this embodiment, the primary winding 52 of the transformer 34 needs only a single winding. The switches 30A, 30B, 30C, 30D remain in a push-pull configuration and, via their associated drivers 32A, 32B, 32C, 32D, apply voltage to alternate ends of the primary of the transformer 34 in anti-phase. The controller 28 controls the flow of the current in the primary of the transformer 34 in opposite directions to create an appropriate current flow in a secondary winding 82 of the transformer 34 and hence the appropriate current flows at the input 24. Also, in the embodiment of FIG. 6, the controller 28 is connected to the control system ground 56 with galvanic isolation 62 provided by the isolated drivers 32A, 32B, 32C, 32D. This configuration may be applied to any of the previous embodiments, if desired, and may remove the need for the galvanic isolation 62 of the trigger input signal 42, output signals 44 and 46, and/or the control signal 72 of those previous embodiments.

Figure 7:
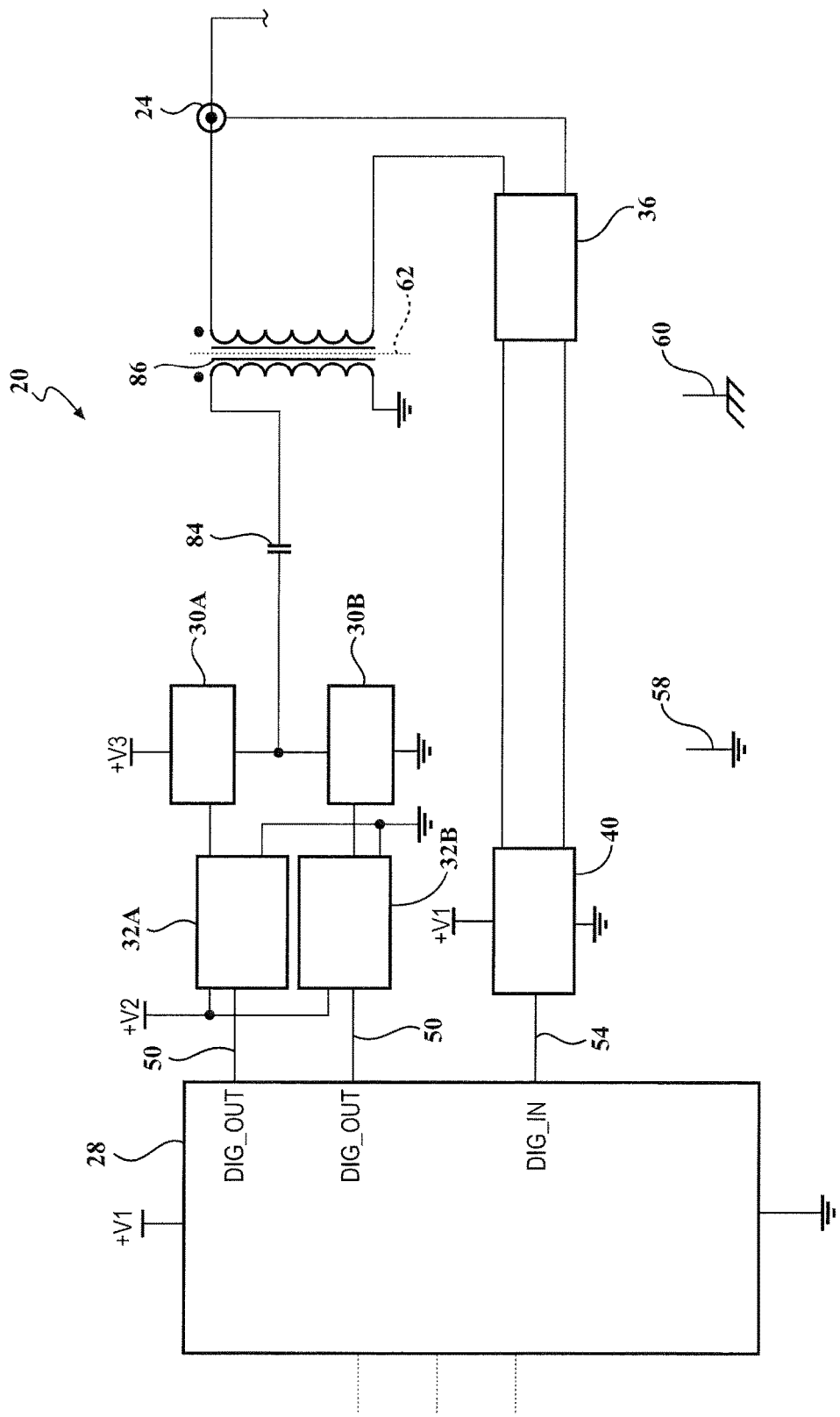
FIG. 7 is a block diagram of a corona discharge ignition system according to a seventh exemplary embodiment of the invention.

A corona ignition system 20 according to another exemplary embodiment is shown in FIG. 7. The system 20 of this embodiment is similar to the system 20 of FIG. 1, except in this case, the transformer 34 is replaced by a capacitor 84 and a balun 86. The balun 86 typically, but not necessarily, has a turns ratio close to 1:1 and is primarily used to match the impedance of the drive circuit (which includes the drivers and switches) to the impedance of the load input 24 to provide improved overall efficiency. Replacing the transformer 34 with the balun 86 typically requires several other changes. For example, the input side of the balun 86 does not limit the DC current flow from the drive circuit, whose average DC voltage will be ½V3. Thus, the capacitor 84 is added to block this current. Second, the balun 86 typically requires a higher voltage because the turns ratio of the balun 86 is typically low, often 1:1, while the transformer 34 may have a turns ratio of 1:3, 1:5, 1:8 or even 1:20. In the system 20 of FIG. 7, the load voltage will be related to + and −½V3 by the turns ratio of the balun 86. The balun 86 can also galvanically isolate the load input 24 from the drive circuit.

Figure 8:
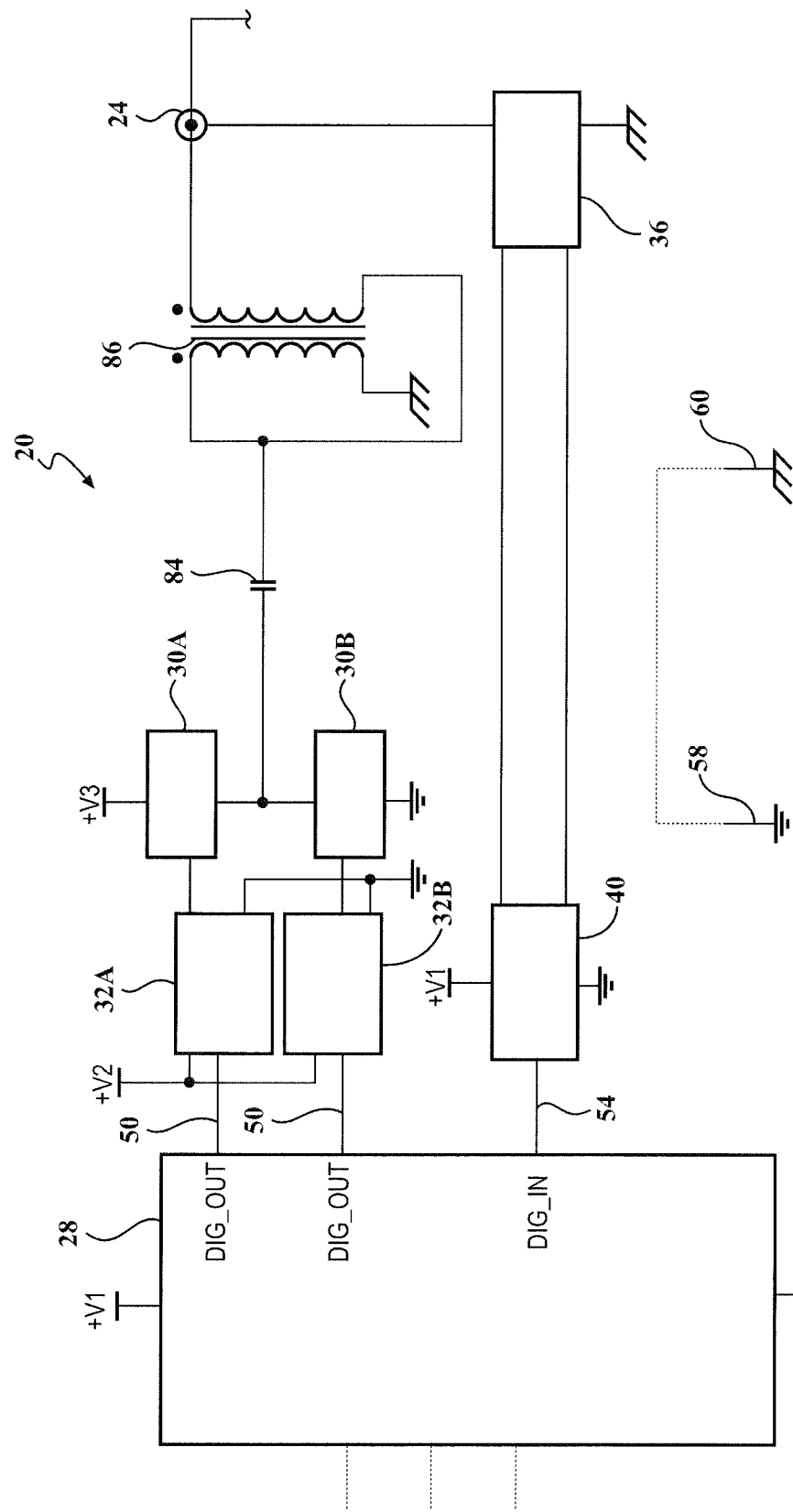
FIG. 8 is a block diagram of a corona discharge ignition system according to an eighth exemplary embodiment of the invention.

FIG. 8 shows an eighth exemplary embodiment, which is similar to FIG. 7 but with a modified connection. In this example, the balun 86 no longer provides isolation. Instead, the balun 86 provides voltage doubling, wherein the voltage applied to the load is related to + and −V3.

Figure 9:
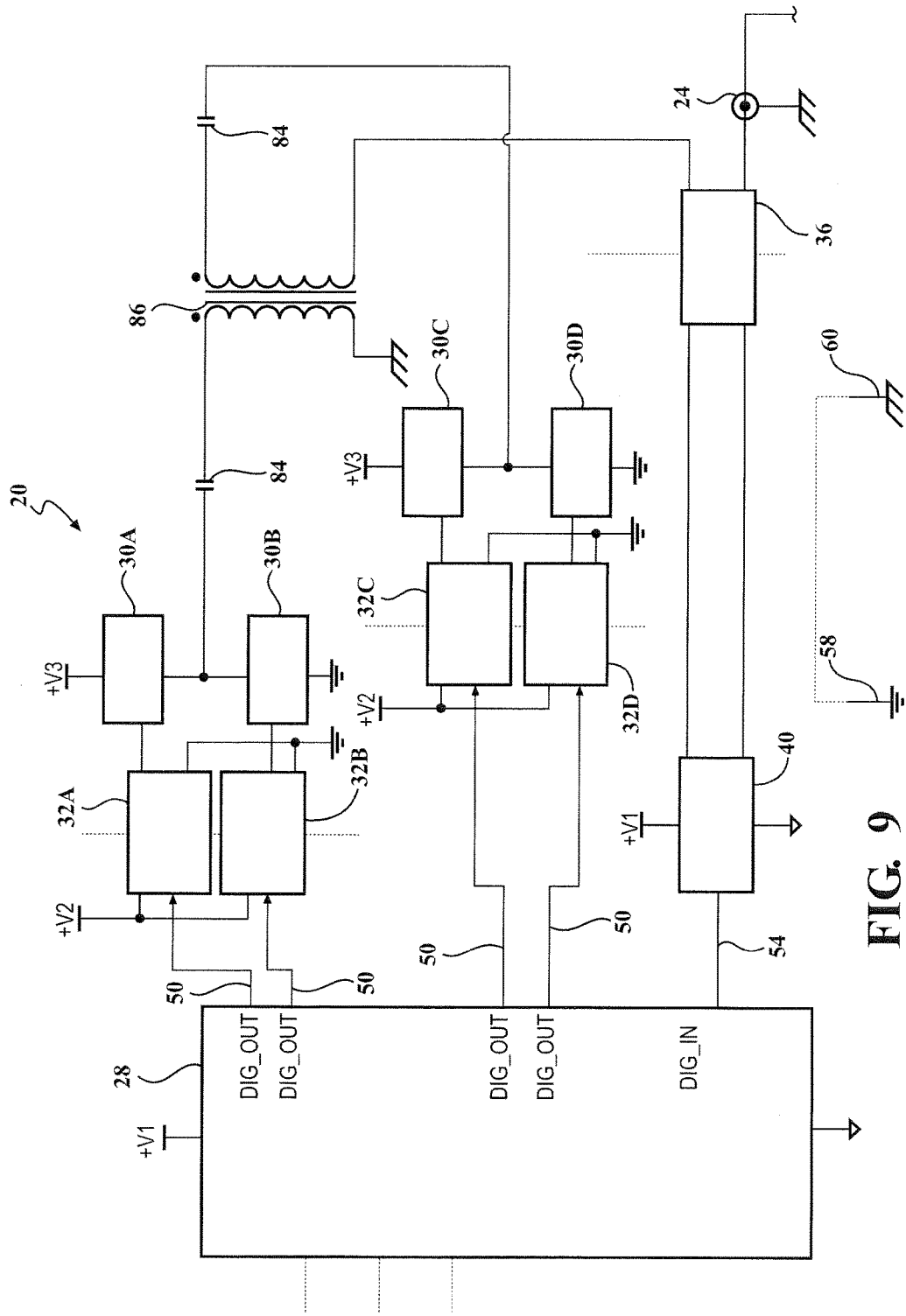
FIG. 9 is a block diagram of a corona discharge ignition system according to a ninth exemplary embodiment of the invention.

FIG. 9 shows a corona ignition system 20 according to a ninth exemplary embodiment. In this embodiment, the four switches 30A, 30B, 30C, 30D are configured as a "full-bridge," and the balun 86 requires two capacitors 84 to block DC current. In addition, the isolating first current sensor 36 measures the current at the high voltage side, also referred to as the "high-side" position. This circuit topology may be implemented in cases where a common mode rejection ratio (CMRR) of the first current sensor 36 is sufficiently high and when the first current sensor 36 is able to safely withstand the high voltages at this circuit location. In addition, the switches 30A, 30B, 30C, 30D of this embodiment allow the circuit to operate in two distinct modes. The first mode is a "full-bridge" mode, wherein the circuit (which includes the drivers and switches) operates similarly to the circuit of FIG. 6. The pairs of switches 30A/30B and 30C/30D are each in the "push-pull" configuration and are driven in anti-phase, such that the voltage applied to the load is related to + and −V3. The second mode keeps one side of the balun 86 permanently grounded, for example by activation of switch 6D. The switches 30A and 30B are then driven in anti-phase to give a single-ended mode of operation where the voltage applied to the load is related to + and −½V3, i.e. one half of the voltage of the "full-bridge" mode. The configuration of FIG. 9 provides a method of voltage control which is not easily available in other topologies.

Figure 10:
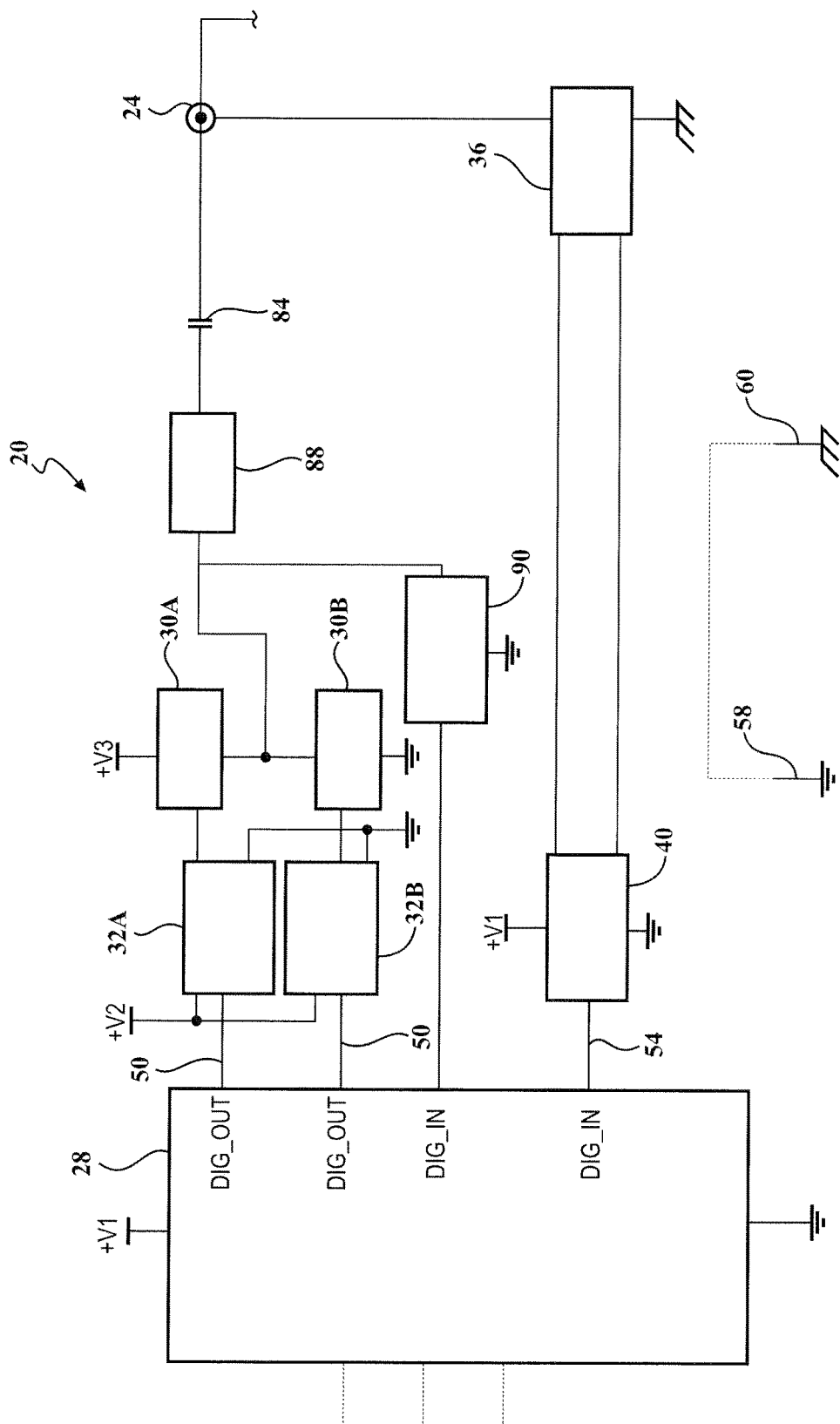
FIG. 10 is a block diagram of a corona discharge ignition system according to a tenth exemplary embodiment of the invention.

FIG. 10 is a block diagram of a corona ignition system 20 according to a tenth exemplary embodiment. In this embodiment, the input 24 is driven directly by the switches 30A, 30B. As in the previous embodiments, the switches 30A, 30B switch between voltage +V3 and ground. However, the system 20 of FIG. 10 does not include a transformer 34 or balun 86 between the switches 30A, 30B and the input 24. Thus, the magnitude of the voltage +V3 provided to the input 24 is increased to make up for the voltage modification typically provided by the transformer 34 or balun 86. The capacitor 84 of FIG. 10 allows AC current to flow through, but blocks DC current which could otherwise flow from the input 24 toward the switches 30A, 30B.

The system 20 of FIG. 10 also optionally includes a frequency filter 88 located between the switches 30A, 30B and the capacitor 84. Alternatively, the frequency filter 88 could be located between the capacitor 84 and the input 24, or the capacitor 84 could be incorporated into the frequency filter 88. The frequency filter 88 is designed to attenuate frequencies above the fundamental or desired frequencies, thus reducing the high frequency components in the output cable (not shown) and reducing electrical noise in the surrounding environment. The frequency filter 88 can also be designed to provide improved impedance, for example an impedance matching the impedance of the load connected to the input 24. An optional second signal conditioner 90 can also be used to sample the phase of the voltage provided to the load at the input 24 by the frequency filter 88. The second signal conditioner 90 typically functions similar to the voltage sensor 78 of FIGS. 4 and 5. For example, the second signal conditioner 90 can obtain the zero crossing of the current. The information about the voltage gathered by the second signal conditioner 90 is provided to the controller 28, and the controller 28 can use the information to correct for delays which occur in the drivers 32A, 32B and switches 30A, 30B. Although FIG. 10 shows the optional second signal conditioner 90 connected to the output of the switches 30A, 30B, the second signal conditioner 90 could alternatively be located at the output of the of the drivers 32A, 32B, or between the frequency filter 88 and the capacitor 84, or between the capacitor 84 and the input 24.

The features of the exemplary systems 20 shown in FIGS. 1-10 may be used in various combinations, other than those specifically described herein. The system 20 of the present invention provides diagnostic and control capabilities which are not possible with the comparative systems, for example those which either attempt to approximate the resonant frequency by making a number of trials at different frequencies and using feedback parameters (e.g. current flow, output voltage, energy consumption) to identify the closest trial to resonance; adjust the resonant frequency to reduce the phase difference between voltage and current over a significant number of resonant cycles; or use a fixed delay, built in to the filter design, to allow resonance over a limited range of frequencies.

As discussed above, the system 20 of the present invention allows near-instantaneous synchronization of the voltage of the circuit to the phase of the current in the load, thus causing the drive frequency to be equal to, or approximately equal to, the resonant frequency of the corona igniter 22. The system 20 also provides the advantage of being able to operate over a wide range of frequencies. The majority of the loop delay is provided by a variable delay implemented in the control software of the controller 28, rather than by a delay built into the hardware, such as in a low-pass filter, as in comparative systems. Typically, the short delay that occurs in the system 20 of the present invention is approximately one half of the period of oscillation, or less than one half of the period of oscillation, and thus allows a wider range of resonant frequencies. Preferably, the phase shift of the current output signal 54 is less than 180 degrees, and more preferably the phase shift is less than 90 degrees, which is less than one half cycle. The short delay also allows the drive frequency to be adjusted to match changes in the resonant frequency almost immediately. The controller 28 is thus able to activate the switches 30A, 30B based on a zero crossing event of the most recent full cycle of the output current, or one of the previous full cycles, allowing additional improvements in control of the drive frequency.

Obviously, many modifications and variations of the present invention are possible in light of the above teachings and may be practiced otherwise than as specifically described while within the scope of the claims.

What is claimed is:

1. A corona discharge ignition system, comprising:
a corona igniter receiving energy at a drive frequency and an output current;
a first switch and a second switch each providing energy to the corona igniter at the drive frequency; and
a controller obtaining an output current signal representative of the output current received by the corona igniter;
the controller activating the first switch an amount of time after a first zero crossing of the output current signal while the second switch is not activated, wherein the first zero crossing is a zero crossing of the most recent full cycle of the output current signal, and the amount of time after the first zero crossing is determined based on at least one zero crossing of at least one full cycle of the output current signal previous to the most recent full cycle.

2. The system of claim 1, wherein the controller activates the second switch an amount of time after a second zero crossing of the output current signal occurring after the first zero crossing, and the first switch is not activated while the second switch is activated.

3. The system of claim 2, wherein the controller deactivates the first switch before activating the second switch.

4. The system of claim 2, wherein the first switch is activated and the second switch is deactivated whenever the output current signal is positive; and the first switch is deactivated and the second switch is activated whenever the output current signal is negative.

5. The system of claim 2, wherein one of the switches is activated by the controller each time the output current received by the corona igniter crosses through zero.

6. The system of claim 2 including a first driver activating the first switch and a second driver activating the second switch in response to drive signals from the controller.

7. The system of claim 1, wherein the amount of time between the first zero crossing of the output current signal and activation of the first switch is provided by an algorithm programmed into the controller.

8. The system of claim 1, wherein the controller determines the amount of time between when the first zero crossing of the output current signal and activation of the first switch by analyzing more than one of the full cycles of the output current signal previous to the most recent full cycle.

9. The system of claim 1, wherein the corona igniter has a resonant frequency, and the drive frequency provided to the corona igniter is equal to the resonant frequency of the corona igniter.

10. The system of claim 1 including a current sensor measuring the output current received by the corona igniter and transmitting the output current signal toward the controller; a filter receiving the output current signal from the current sensor and creating a phase shift of not greater than 180 degrees in the output current signal before transmitting the output current signal toward the controller.

11. The system of claim 1 including a transformer between the switches and the corona igniter.

12. The system of claim 11 including a voltage sensor between the transformer and the controller.

13. The system of claim 1 including a capacitor and a balun between the switches and the corona igniter.

14. A method of controlling a corona discharge ignition system, the system including a corona igniter receiving energy at a drive frequency and an output current, and a first switch and a second switch for providing energy to the corona igniter at the drive frequency, comprising the steps of:
obtaining an output current signal representative of the output current received by the corona igniter; and
activating the first switch an amount of time after a first zero crossing of the output current signal while the second switch is not activated, and wherein the first zero crossing is a zero crossing of the most recent full cycle of the output current signal, and the amount of time after the first zero crossing is determined based on at least one zero crossing of at least one full cycle of the output current signal previous to the most recent full cycle.

15. The method of claim 14 including activating the second switch an amount of time after a second zero crossing of the output current signal occurring after the first zero crossing, and wherein the first switch is not activated while the second switch is activated.

16. The method of claim 15 including activating one of the switches each time the output current received by the corona igniter crosses through zero.

17. The method of claim 15, wherein the first switch is activated and the second switch is deactivated whenever the output current signal is positive; and the first switch is deactivated and the second switch is activated whenever the output current signal is negative.

18. The method of claim 15 including deactivating the first switch before activating the second switch.

19. The method of claim 14 including obtaining the amount of time between the first zero crossing and activating the first switch by analyzing more than one of the full cycles of the output current signal previous to the most recent full cycle.

20. The method of claim 14, wherein the corona igniter has a resonant frequency, and the drive frequency is equal to the resonant frequency of the corona igniter.

* * * * *